United States Patent [19]

Matsui et al.

[11] Patent Number: 4,772,627
[45] Date of Patent: Sep. 20, 1988

[54] GROUND MIXTURE

[75] Inventors: Masakazu Matsui; Shigeharu Yokohama; Toshio Kashihara, all of Osaka, Japan

[73] Assignee: Takeda Chemical Industries, Ltd., Osaka, Japan

[21] Appl. No.: 3,612

[22] Filed: Jan. 15, 1987

Related U.S. Application Data

[63] Continuation of Ser. No. 623,196, Jun. 21, 1984, abandoned.

[30] Foreign Application Priority Data

Jun. 28, 1983 [JP] Japan ................................. 58-117906
Jun. 8, 1984 [JP] Japan ................................. 59-118697

[51] Int. Cl.$^4$ ........................ A61K 47/00; A61K 9/14
[52] U.S. Cl. .................................. 514/462; 514/772; 514/789; 514/951; 424/125; 424/489
[58] Field of Search ............... 514/462, 772, 789, 951; 424/125, 489

[56] References Cited

U.S. PATENT DOCUMENTS

| | | | |
|---|---|---|---|
| 691,255 | 1/1902 | Fox | 424/125 |
| 1,170,056 | 2/1916 | Engelmann | 424/489 |
| 2,037,090 | 4/1936 | Pough | 424/125 |
| 2,900,304 | 8/1959 | Martin | 514/462 |
| 3,330,727 | 7/1967 | Lees | 514/462 |
| 3,642,986 | 2/1972 | Welch et al. | 424/125 |
| 3,922,354 | 11/1975 | Galluzzi et al. | 426/516 |
| 3,966,899 | 6/1976 | Nakai et al. | 514/778 |
| 3,972,999 | 8/1976 | Tsuk | 424/78 |
| 4,001,434 | 1/1977 | Nakai et al. | 514/777 |
| 4,344,934 | 8/1982 | Martin et al. | 424/80 |
| 4,486,436 | 12/1984 | Sunshine et al. | 514/263 |

FOREIGN PATENT DOCUMENTS

| | | | |
|---|---|---|---|
| 987588 | 4/1976 | Canada. | |
| 2808311 | 9/1979 | Fed. Rep. of Germany | 424/125 |
| 59-139322 | 8/1984 | Japan | 424/125 |
| 311235 | of 1930 | United Kingdom | 424/125 |
| 1327853 | 8/1973 | United Kingdom. | |

OTHER PUBLICATIONS

Chem. Pharm. Bull. 26 (10) 2983–2989 (1978).
Journal of Pharmacokinetics and Biopharmaceutics, vol. 2, No. 6, 1974 pp. 487–493.
The United States Pharmacopeia, twentieth revision, United States Pharmacopeial Convention, Inc., Rockville, MD 1979, pp. 359–360.
Abdallah et al., "Influence of Dispersion Method on Particle Size and Dissolution of Griseofulvin–silicon Dioxide Triturations", *Drug Development and Industrial Pharmacy*, 9(5), 795–808, (1983).
McGinity et al., "Increasing Dissolution Rates of Poorly Soluble Drugs by Adsorption to Montmorillonite" *Drug Development and Industrial Pharmacy*, 6(1), 35–48 (1980).
Monkhouse et al., "Use of Adsorbents in Enhancement of Drug Dissolution I", *Journal of Pharmaceutical Sciences*, vol. 61, No. 9, pp. 1430–1435, (1972).
Yang et al., "Effects of Amorphous Silicon Dioxides on Drug Dissolution", *Journal of Pharmaceutical Sciences*, vol. 68, No. 5 (1979).

*Primary Examiner*—Ronald W. Griffin
*Attorney, Agent, or Firm*—Wegner & Bretschneider

[57] ABSTRACT

A ground mixture of a poorly soluble crystalline drug and an adsorbent is remarkably improved in the rates of dissolution and adsorption of the drug.

9 Claims, 2 Drawing Sheets

GROUND MIXTURE

This application is a continuation of Ser. No. 623,196, filed June 21, 1984, now abandoned.

This invention relates to a ground mixture. More particularly, the invention relates to a ground mixture of a poorly soluble crystalline drug and an adsorbent.

Attempts have so far been made to improve the absorption of poorly soluble drugs (1) by forming their water-soluble salts, (2) by reducing their particle size by grinding, for instance, or (3) by grinding together with β-1,4-glucan[Japanese Patent Examined Publication No. 29565/1979: Journal of Pharmacokinetics and Biopharmaceutics Vol. 2, 487–493 (1974)]. However, each method has its problems, hence cannot be said to be satisfactory. For instance, (1) The conversion of poorly soluble drugs into the form of salts which are readily soluble in water may often result in changes in pharmacological effects; it is not possible to convert all poorly soluble drugs into water soluble salts which have high pharmacological effects but few adverse effects.

(2) Although it is said that particle size reduction by grinding or the like increases solubility of poorly soluble drugs and thereby improves their absorption, the fact of the matter is that the results are unsatisfactory in many cases, with not a few problems from the pharmaceutical engineering viewpoints. Thus, in pulverizing granular drug alone under the action of a mechanical force, the grinding efficiency is in general low and much time is required for grinding. Some drugs are even degraded by the heat generated during a long period of grinding.

(3) Attempts to improve the absorption of poorly soluble drugs by rendering them noncrystalline by grinding together with β-1,4-glucan are found in a number of reports. However, in practicing this method, the additive (β-1,4-glucan) is required in proportions [additive/(additive+drug)] as high as 80–90% for rendering the drug noncrystalline form. The use of said method is therefore inadequate in cases where the drugs are to be administered in high unit doses. Furthermore, it is necessary to carry out the grinding in a vibrating mill for a period in the order of several hours and, therefore, much labor is required in this process.

As a result of intensive research conducted to produce improvements in absorption of poorly soluble drugs, the inventors have completed the present invention.

Figure 1:
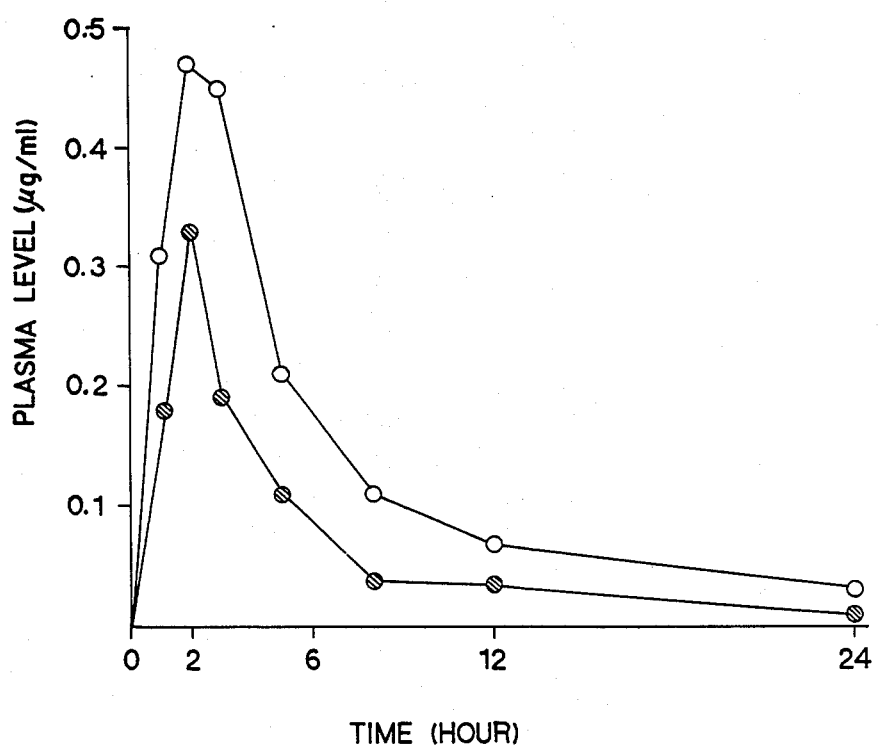
FIG. 1 represents the beagle plasma griseofulvin level curves obtained in Test Example 5. Thus o—o and ●—● depict the beagle plasma griseofulvin levels after oral administration of the ground mixture and griseofulvin per se, respectively.

Thus, the invention provides a ground mixture of a poorly soluble crystalline drug and an adsorbent.

One preferred embodiment of the poorly soluble crystalline drug to be used in the practice of the invention includes such compounds as acetylspiramycin, aminopyrine, estradiol benzoate, ampicillin, ethynylestradiol, erythromycin, quinine hydrochloride, caffeine, camphor, kitasamycin, griseofulvin, calcium gluconate, chloramphenicol, cortisone acetate, salicylic acid, digitoxin, theophylline, mystatin, hydrocortisone, phenobarbital, prednisolone, progesterone, methylestosterone, riboflavin and colistin sulfate. As desired, two or more drugs may be subjected simultaneously to grinding.

Another preferred embodiment of the poorly soluble crystalline drug to be used in the practice of the invention is a poorly soluble crystalline drug having an isoflavone moiety.

According to this invention, a ground mixture of the latter embodiment and an adsorbent is more remarkably improved in the rate of absorption of the drug than a ground mixture of the former and an adsorbent.

The poorly soluble crystalline drug having an isoflavone moiety to be used in the practice of this invention is a drug which is poorly soluble in water and crystalline and has an isoflavone moiety, and is preferred a compound of the formula

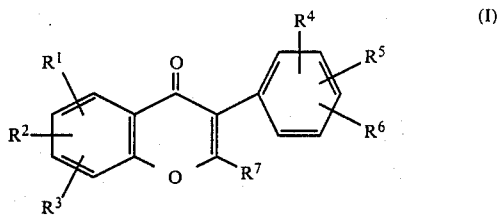

wherein
$R^1$, $R^2$ and $R^3$ are independently hydrogen, hydroxy, alkoxy, aralkyloxy, acyloxy or alkyl,
$R^4$, $R^5$ and $R^6$ are independently hydrogen, halogen, hydroxy, alkoxy, alkyl, amino, nitro, aryl or alkylsulfonyloxy, and
$R^7$ is hydrogen, hydroxy, alkoxy, alkyl, carboxyl or alkoxycarbonyl.

Referring to the formula (I), the alkoxy group represented by $R^1$, $R^2$ or $R^3$ is exemplified by $C_{1-6}$ alkoxy such as methoxy, ethoxy, propoxy, isopropoxy, butoxy, pentyloxy or hexyloxy. The said alkoxy group may be substituted by such a group as carboxy, lower($C_{1-4}$)alkoxycarbonyl (e.g. methoxycarbonyl, ethoxycarbonyl), carbamoyl, N-[lower($C_{1-4}$)alkyl]carbamoyl (e.g. N-methylcarbamoyl), N,N-[di-lower($C_{1-4}$)alkyl]carbamoyl (e.g. N,N-dimethylcarbamoyl), hydroxy, lower($C_{1-4}$)alkoxy (e.g. methoxy, ethoxy), N-[N,N-di-lower($C_{1-4}$)alkylamino]ethyl-carbamoyl [e.g. (N,N-dimethylamino)ethylcarbamoyl], piperidinocarbonyl, morpholinocarbonyl or [di-($C_{1-4}$)alkyl]amino (e.g. dimethylamino). The said substituted alkoxy group is exemplified by a group such as carboxymethoxy, methoxycarbonylmethoxy, ethoxycarbonylmethoxy, carbamoylmethoxy, (N-methylcarbamoyl)methoxy, (N,N-dimethylcarbamoyl)methoxy, piperidinocarbonylmethoxy, morpholinocarbonylmethoxy, N-(dimethylaminoethyl)carbamoylmethoxy, 2-hydroxyethoxy, 2-dimethylaminoethoxy, 1-carboxyethoxy, 1-ethoxycarbonylethoxy or 1-ethoxycarbonylpropoxy.

The aralkyloxy group represented by $R^1$, $R^2$ or $R^3$ is exemplified by phenyl-lower($C_{1-4}$)alkoxy such as benzyloxy. The phenyl group of the said phenyl-lower alkoxy group may be substituted by a group such as halogen (e.g. chlorine) or amino. The said substituted-phenyl-lower alkoxy group is exemplified by 4-chlorobenzyloxy or 4-aminobenzyloxy.

The acyloxy group represented by $R^1$, $R^2$ or $R^3$ is exemplified by lower($C_{1-4}$)alkanoyloxy or alkenoyloxy which is substituted by lower($C_{1-4}$)alkoxy carbonyl, such as 3-ethoxycarbonylpropionyloxy or 3-ethoxycarbonylacryloyloxy.

The alkoxy group represented by $R^4$, $R^5$, $R^6$ or $R^7$ is exemplified by $C_{1-4}$ alkoxy such as methoxy, ethoxy, propoxy, isopropoxy or butoxy.

The halogen represented by $R^4$, $R^5$ or $R^6$ is exemplified by fluorine, bromine or iodine and the aryl group represented by $R^4$, $R^5$ or $R^6$ is exemplified by phenyl. The alkylsulfonyloxy group represented by $R^4$, $R^5$ or $R^6$ is exemplified by lower($C_{1-4}$)alkylsulfonyloxy such as methylsulfonyloxy.

The alkoxycarbonyl group represented by $R^7$ is exemplified by lower($C_{1-4}$)alkoxycarbonyl such as methoxycarbonyl or ethoxycarbonyl.

The represented compounds of the formula (I) are disclosed below:

(1) 2-Carboxy-7-ethoxycarbonyl-3-phenyl-4H-1-benzopyran-4-one
(2) 2-Ethoxycarbonyl-5,7-dihydroxy-3-phenyl-4H-1-benzopyran-4-one
(3) 7-Ethoxy-3-phenyl-4H-1-benzopyran-4-one
(4) 5,7-Dihydroxy-3-phenyl-4H-1-benzopyran-4-one
(5) 7-Ethoxy-2-ethoxycarbonyl-5-hydroxy-3-phenyl-4H-1-benzopyran-4-one
(6) 7-Ethoxycarbonylmethoxy-2-methyl-3-phenyl-4H-1-benzopyran-4-one
(7) 7-Ethenyloxycarbonylmethoxy-2-methyl-3-phenyl-4H-1-benzopyran-4-one
(8) 7-Carbamoylmethoxy-2-methyl-3-phenyl-4H-1-benzopyran-4-one
(9) 7-(N-Methylcarbamoyl)methoxy-2-methyl-3-phenyl-4H-1-benzopyran-4-one
(10) 7-(N,N-Dimethylcarbamoyl)methoxy-2-methyl-3-phenyl-4H-1-benzopyran-4-one
(11) 7-Piperidinocarbonylmethoxy-2-methyl-3-phenyl-4H-1-benzopyran-4-one
(12) 7-Morpholinocarbonylmethoxy-2-methyl-3-phenyl-4H-1-benzopyran-4-one
(13) 7-[N-(N,N-Dimethylaminoethyl)carbamoyl]methoxy-2-methyl-3-phenyl-4H-1-benzopyran-4-one
(14) 7-Ethoxycarbonylmethoxy-2-methyl-3-(4-chlorophenyl)-4H-1-benzopyran-4-one
(15) 7-Ethoxycarbonylmethoxy-2-butyl-3-phenyl-4H-1-benzopyran-4-one
(16) 7-Ethoxycarbonylmethoxy-2-methyl-3-(4-aminophenyl)-4H-1-benzopyran-4-one
(17) 7-Ethoxycarbonylmethoxy-3-phenyl-4H-1-benzopyran-4-one
(18) 7-Carbamoylmethoxy-3-phenyl-4H-1-benzopyran-4-one
(19) 7-Ethoxycarbonylmethoxy-3-(4-chlorophenyl)-4H-1-benzopyran-4-one
(20) 7-Ethoxycarbonylmethoxy-3-(p-tolyl)-4H-1-benzopyran-4-one
(21) 7-Ethoxycarbonylmethoxy-2-methyl-3-(p-tolyl)-4H-1-benzopyran-4-one
(22) 7-Hydroxy-3-phenyl-4H-1-benzopyran-4-one
(23) 7-Isopropoxy-3-phenyl-4H-1-benzopyran-4-one
(24) 7-Hexyloxy-3-phenyl-4-H-1-benzopyran-4-one
(25) 7-Benzyloxy-2-methyl-3-phenyl-4H-1-benzopyran-4-one
(26) 7-(4-Chlorobenzyl)oxy-3-phenyl-4H-1-benzopyran-4-one
(27) 7-(4-Nitrobenzyl)oxy-2-methyl-3-phenyl-4H-1-benzopyran-4-one
(28) 7-(2-Hydroxyethoxy)-3-phenyl-4H-1-benzopyran-4-one
(29) 7-Hydroxy-3-(4-hydroxyphenyl)-4H-1-benzopyran-4-one
(30) 3-Phenyl-4H-1-benzopyran-4-one
(31) 2,7-Dihydroxy-3-(3,4-dihydroxyphenyl)-4H-1-benzopyran-4-one
(32) 5,7-Dihydroxy-3-(4-hydroxyphenyl)-4H-1-benzopyran-4-one
(33) 5,6-Dihydroxy-7-methoxy-3-(5-hydroxy-3,4-dimethoxyphenyl)-4H-1-benzopyran-4-one
(34) 2,5,6,7-Tetramethoxy-3-(3,4-dimethoxyphenyl)-4H-1-benzopyran-4-one
(35) 7-(2-Ethoxycarbonylethoxy)-2-methyl-3-(3,4-dimethoxyphenyl)-4H-1-benzopyran-4-one
(36) 7-(2-Ethoxyethoxy)-3-phenyl-4H-1-benzopyran-4-one
(37) 7-Hexyloxy-2-methyl-3-phenyl-4H-1-benzopyran-4-one
(38) 7-Ethoxycarbonylmethoxy-3-(4-hydroxyphenyl)-4H-1-benzopyran-4-one
(39) 7-Carboxymethoxy-3-(4-hydroxyphenyl)-4H-1-benzopyran-4-one
(40) 7-(3-Ethoxycarbonylpropionyloxy)-3-(4-hydroxyphenyl)-4H-1-benzopyran-4-one
(41) 7-(3-Ethoxycarbonylacryloyloxy)-3-(4-hydroxyphenyl)-4H-1-benzopyran-4-one
(42) 7-(2-Dimethylaminoethoxy)-3-(4-hydroxyphenyl)-4H-1-benzopyran-4-one
(43) 7-(1-Ethoxycarbonylpropoxy-3-(4-hydroxyphenyl)-4H-1-benzopyran-4-one
(44) 7-Hydroxy-3-(4-methoxyphenyl)-4H-1-benzopyran-4-one
(45) 5,7-Dimethyl-3-(4-methoxyphenyl)-4H-1-benzopyran-4-one
(46) 5-Hydroxy-7-methyl-3-(4-hydroxyphenyl)-4H-1-benzopyran-4-one
(47) 7-Hydroxy-5-methyl-3-(4-hydroxyphenyl)-4H-1-benzopyran-4-one
(48) 5-Hydroxy-7-methyl-3-(3-chlorophenyl)-4H-1-benzopyran-4-one
(49) 5,7-Dimethoxy-3-(3-chlorophenyl)-4H-1-benzopyran-4-one
(50) 5,7-Dihydroxy-3-(4-methoxyphenyl)-4H-1-benzopyran-4-one
(51) 5,7-Dihydroxy-3-(4-fluorophenyl)-4H-1-benzopyran-4-one
(52) 5,7-Dihydroxy-3-(4-bromophenyl)-4H-1-benzopyran-4-one
(53) 5,7-Dihydroxy-3-(4-nitrophenyl)-4H-1-benzopyran-4-one
(54) 5,7-Dihydroxy-3-phenyl-4H-1-benzopyran-4-one
(55) 5,7-Dihydroxy-3-(4-biphenyl)-4H-1-benzopyran-4-one
(56) 5,7-Dihydroxy-3-(4-methylsulfonyloxyphenyl)-4H-1-benzopyran-4-one
(57) 2-Ethoxycarbonyl-7-ethoxycarbonylmethoxy-3-phenyl-4H-1-benzopyran-4-one
(58) 2-Carboxy-7-carboxymethoxy-3-phenyl-4H-1-benzopyran-4-one
(59) 5,7-Bis(ethoxycarbonylmethoxy)-2-ethoxycarbonyl-3-phenyl-4H-1-benzopyran-4-one
(60) 2-Ethoxycarbonyl-7-(1-ethoxycarbonylethoxy)-3-phenyl-4H-1-benzopyran-4-one

(61) 7-Isopropoxy-3-(4-hydroxyphenyl)-4H-1-benzopyran-4-one [melting point: 184°–185° C.]

(62) 7-(1-Carboxyethoxy)-3-phenyl-4H-1-benzopyran-4-one [melting point: 223° C.]

(63) 7-(1-Carboxyethoxy)-3-(4-hydroxyphenyl)-4H-1-benzopyran-4-one [melting point: 201°–202° C.]

(64) 7-(1-Carboxyethoxy)-3-(3-hydroxyphenyl)-4H-1-benzopyran-4-one [melting point: 218°–219° C.]

Compounds (1) to (60), their production and utilities are described in literature references such as U.S. Pat. No. 3,352,754, British Patent Publication No. 953978, French Special Patent for Medicament 1065, Japanese Patent Examined Publication No. 13391/1979, Japanese Patent Unexamined Publication No. 46217/1984, Japanese Patent Unexamined Publication No. 50657/1978, Japanese Patent Examined Publication No. 32074/1972, Japanese Patent Unexamined Publication No. 57182/1977 and Belgian Pat. No. 2190411.

Methods of producing Compound (61) and Compounds (62) to (64) as well as their use for treatment of osteoporosis are described in Japanese Patent Application No. 163914/1983 filed on Sept. 15, 1983 and Japanese Patent Application No. 242779/1983 filed on Dec. 21, 1983, respectively.

As the adsorbent to be used in accordance with the invention, there may be used any adsorbent, but preferred is an adsorbent which has an adsorption ability of not less than 0.15 $cm^3/g$ as measured by the methanol adsorption method in view of a small amount of an adsorbent to be used and short grinding time. Such adsorbent includes activated charcoal, activated clay, silica, synthetic adsorbent resin, activated alumina and other physiologically acceptable adsorbents. These adsorbents may be used either singly or in combination of two or more. It is advantageous to use an adsorbent preferably having an adsorption ability of 0.15 $cm^3/g$ to 1.50 $cm^3/g$, though depending on the poorly soluble drug, the apparatus for grinding, the ratio of addition of the adsorbent and the grinding time.

The methanol adsorption method is one of methods conventionally used in determining the micropore volume of a material having micropores such as activated charcoal, silica gel, alumina or silica alumina. In the present invention, the volume ($cm^3$) of methanol (on the liquid basis) adsorbed on each gram of the adsorbent under the conditions of relative pressure$=0.937$ and temperature$=25°$ C. is defined as the adsorption ability measured by the methanol adsorption method ($cm^3/g$). As the apparatus to be used in determining the adsorption ability, there may be used such a known apparatus as an automatic adsorption-measuring apparatus which directly measures, the gravimetric method, the change in weight upon passing a mixed gas composed of methanol and nitrogen through the adsorbent suspended on a quartz spring device, or an automatic adsorption-measuring apparatus which records the change in weight using a differential transformer provided with a feedback coil. An apparatus used in carrying out the nitrogen adsorption method, one of the methods of measuring the surface area of a material having micropores, may also be used in determining the adsorption ability of methanol.

The adsorbent is used generally at an addition level [adsorbent/(adsorbent+poorly soluble crystalline drug)] of about 20–60% (w/w), preferably about 30–50%.

As the grinding apparatus, there may be employed any apparatus which is capable of achieving grinding in accordance with the invention, although a vibrating mill, for instance, is preferred.

The time required for grinding depends on the poorly soluble crystalline drug, the adsorbent, the grinding apparatus and the ratio of the adsorbent to be added but is sufficient if X-ray powder diffractometry after grinding does not give any diffraction peaks characteristic of a crystalline substance any more. Generally, grinding is performed for about 30 seconds to about an hour.

The poorly soluble crystalline drug and the adsorbent may either be subjected, as they are, to grinding following admixture of them or be subjected, after preliminary grinding of each, to grinding following admixture thereof.

In the ground mixture obtained by the method according to the invention, the drug is in the amorphous state, so that the mixture is remarkably improved in the rates of dissolution and absorption of the drug, in particular, in the rate of absorption following oral administration.

The ground mixture according to the invention may be used either per se or in admixture with one or more pharmacologically acceptable carriers, excipients, and so forth, in formulations such as powders, granules, tablets, pills, capsules, ointment, or some other appropriate preparation. The mixture thus can be administered orally or percutaneously to human and other animals with a particular disease to be treated with the drug.

The invention is further illustrated in more detail by the following examples and test examples, which, however, are by no means limitative of the present invention.

EXAMPLE 1

Two g of AEROSIL ® (ultramicroparticulate silicic anhydride) [Aerosil Nippon, Japan] having an adsorption ability of 0.21 $cm^3/g$ as measured by the methanol adsorption method and 2 g of griseofulvin were charged in a stainless steel vibrating mill (50 cc in capacity; with two balls each 2.7 mm in diameter) [Spex Industries Inc., USA], and were ground together for 30 minutes.

The crystallinity of the griseofulvin in the ground mixture was measured using a recording X-ray diffractometer [Model D-3F; Rigaku Denki]. No peaks indicating the crystallinity of griseofulvin were observed.

X-Ray diffractometry conditions:

| Target: Cu; Filter: Ni; | [ kV: kilovolt ] |
| Voltage: 40 kV; Current: 30 mA. | [ mA: milliampere ] |

EXAMPLE 2

Two g of activated charcoal [adsorbency for methanol: 0.66 $cm^3/g$] and 2 g of griseofulvin were ground together for 30 seconds in the same manner as Example 1.

X-Ray diffractometry of the ground mixture under the same measurement conditions as in Example 1 gave no peaks.

EXAMPLE 3

Two g of AEROSIL and 2 g of chloramphenicol were ground together for 30 minutes in the same manner as Example 1.

X-Ray diffractometry of the ground mixture gave no peak due to the crystalline chloramphenicol.

EXAMPLE 4

Two g of AEROSIL and 2 g of theophylline were ground together for 30 minutes in the same manner as Example 1.

X-Ray diffractometry of the ground mixture failed to reveal any peaks due to the presence of crystalline theophylline.

EXAMPLE 5

Two g of AEROSIL and 2 g of 7-isopropoxy-3-phenyl-4H-1-benzopyran-4-one were charged in a stainless steel vibrating mill (50 cc in capacity; with two balls each 2.7 mm in diameter) [Spex Industries Inc., USA] and were ground together for 10 minutes.

EXAMPLE 6

Two g of activated charcoal [Wako Pure Chemicals, Japan] and 2 g of 7-isopropoxy-3-phenyl-4H-1-benzopyran-4-one were ground together for 3 minutes in the same manner as Example 5.

EXAMPLE 7

Two g of activated clay [Wako Pure Chemicals, Japan] and 2 g of 7-isopropoxy-3-phenyl-4H-1-benzopyran-4-one were ground together for 30 minutes in the same manner as Example 5.

EXAMPLE 8

Two g of activated alumina [Wako Pure Chemicals, Japan] and 2 g of 7-isopropoxy-3-phenyl-4H-1-bnezopyran-4-one were ground together for 60 minutes in the same manner as Example 5.

TEST EXAMPLE 1

In a 1,000-cc beaker, there was placed 40 mg of the ground mixture of AEROSIL and griseofulvin as obtained in Example 1 and, then, 900 ml of water was poured into the beaker. The contents were stirred in a water bath adjusted to 37±0.1° C. by rotating a stirrer at a constant speed of revolution, while sampling was conducted at appropriate intervals. Each sample was filtered through a glass filter for removal of AEROSIL. The absorbance at the wavelength of 295 nm was measured using a Hitachi Model 124 U.V. spectrophotometer, and obtained the amount dissolved of griseofulvin from the standard curve.

On the other hand, griseofulvin alone was ground, and 2 g of the ground mass was mixed with 2 g of AEROSIL. A 40-mg portion of the resulting mixture (physical mixture) was subjected to the same test as above and the amount dissolved of griseofulvin was determined.

The results of both tests are given in Table 1.

TABLE 1

| Time (minutes) | Amount dissolved (μg/ml) | |
|---|---|---|
| | Ground mixture | Physical mixture |
| 10 | 6.0 | 1.4 |
| 30 | 10.8 | 2.8 |
| 60 | 12.8 | 3.8 |

As is evident from Table 1, the dissolution of griseofulvin, after 10 minutes, was about 4 times greater and, after 60 minutes, about 3 times greater with the ground mixture was compared with the physical mixture.

TEST EXAMPLE 2

For the ground mixture of activated charcoal and griseofulvin as obtained in Example 2, the griseofulvin dissolution was determined in accordance with the method of Test Example 1.

Separately, griseofulvin alone was ground, and a physical mixture of the ground mass and activated charcoal (1:1 by weight) was prepared and tested for griseofulvin dissolution in accordance with the method of Test Example 1.

The results of both tests are shown in Table 2.

TABLE 2

| Time (minutes) | Amount dissolved (μg/ml) | |
|---|---|---|
| | Ground mixture | Physical mixture |
| 10 | 7.8 | 2.0 |
| 30 | 9.0 | 3.6 |
| 60 | 9.2 | 4.6 |

As is evident from Table 2, the dissolution of griseofulvin was about 4 times and about twice more rapid with the ground mixture after 10 minutes and 60 minutes, respectively, as compared with the physical mixture.

TEST EXAMPLE 3

A 800-mg portion of the ground mixture obtained in Example 3 and a 800-mg portion of a physical mixture prepared from 2 g of singly ground chloramphenicol and 2 g of AEROSIL were subjected to the same dissolution test as in Test Example 1. The dissolution was measured by absorbance measurement for each glass filter filtrate on an ultraviolet spectrophotometer at wavelength 278 nm from a standard curve.

The results for both cases are shown in Table 3.

TABLE 3

| Time (minutes) | Amount dissolved (μg/ml) | |
|---|---|---|
| | Ground mixture | Physical mixture |
| 10 | 200 | 80 |
| 30 | 272 | 148 |
| 60 | 360 | 180 |

As is evident from Table 3, the dissolution of chloramphenicol was about 2.5 times and about twice more rapid with the ground mixture after 10 minutes and 60 minutes, respectively, as compared with the physical mixture.

TEST EXAMPLE 4

The ground mixture (1.6 g) obtaied in Example 4 and a physical mixture (1.6 g) prepared from singly ground theophylline and AEROSIL (1:1 by weight) were subjected to a dissolution test in 0.1N aqueous hydrochloric acid. Each glass filter filtrate was assayed for theophylline by absorption spectrophotometry in the 270-nm wavelength.

The results for both mixtures are given in Table 4.

TABLE 4

| Time (minutes) | Amount dissolved (μg/ml) | |
|---|---|---|
| | Ground mixture | Physical mixture |
| 10 | 510 | 136 |

TABLE 4-continued

| Time (minutes) | Amount dissolved (μg/ml) | |
|---|---|---|
| | Ground mixture | Physical mixture |
| 30 | 620 | 296 |
| 60 | 780 | 488 |

As is evident from Table 4, the dissolution from the ground mixture was about 3 times and about twice more rapid after 10 minutes and 60 minutes, respectively, as compared with the physical mixture.

TEST EXAMPLE 5

The ground mixture of AEROSIL and griseofulvin obtained in Example 1 was administered orally to 4 beagles in a dose of 1 g, and plasma griseofulvin levels were determined using a liquid chromatograph (Shimadzu Seisakusho Ltd., Japan).

Separately, griseofulvin alone was administered orally to 4 beagles in a dose of 500 mg, and plasma griseofulvin levels were determined in the same manner as above.

The results of both tests are given in FIG. 1.

As is evident from FIG. 1, the area under the blood level curve (A.U.C.) for the ground mixture was about twice as large as the drug alone.

TEST EXAMPLE 6

In a 1,000 ml beaker, there was placed 40 mg of the ground mixture of AEROSIL and 7-isopropoxy-3-phenyl-4H-1-benzopyran-4-one as obtained in Example 5 and, then, 900 ml of 50% methanol was poured into the beaker. The contents were stirred in a water bath adjusted to 37±0.1° C. by rotating a stirrer at a constant speed of revolution, while sampling was conducted at appropriate intervals. Each sample was filtered through a glass filter for removal of AEROSIL. The absorbance at the wavelength of 248 nm was measured using a Hitachi Model 124 U.V. spectrophotometer, and obtained the amount dissolved of 7-isopropoxy-3-phenyl-4H-1-benzopyran-4-one from the standard curve.

On the other hand, 2 g of 7-isopropoxy-3-phenyl-4H-1-benzopyran-4-one was mixed with 2 g of AEROSIL. The resulting mixture (physical mixture) was subjected to the same test as above and the amount dissolved of 7-isopropoxy-3-phenyl-4H-1-benzopyran-4-one was determined.

The results of both tests are given in Table 5.

TABLE 5

| Time (minutes) | Amount dissolved (μg/ml) | |
|---|---|---|
| | Ground mixture | Physical mixture |
| 10 | 19.0 | 8.2 |
| 30 | 20.4 | 15.0 |

As is evident from Table 5, the dissolution of 7-isopropoxy-3-phenyl-4H-1-benzopyran-4-one was greater with the ground mixture as compared with the physical mixture.

TEST EXAMPLE 7

The ground mixture of AEROSIL and 7-isopropoxy-3-phenyl-4H-1-benzopyran-4-one obtained in Example 5 was administered orally to 4 beagles in a dose of 400 mg, and plasma levels of 7-hydroxy-3-phenyl-4H-1-benzopyran-4-one which was the main metabolite of 7-isopropoxy-3-phenyl-4H-1-benzopyran-4-one were determined using a liquid chromatograph (Shimadzu Seisakusho Ltd., Japan).

Separately, 7-isopropoxy-3-phenyl-4H-1-benzopyran-4-one alone was administered orally to 4 beagles in a dose of 200 mg, and plasma levels of 7-hydroxy-3-phenyl-4H-1-benzopyran-4-one were determined in the same manner as above.

Figure 2:
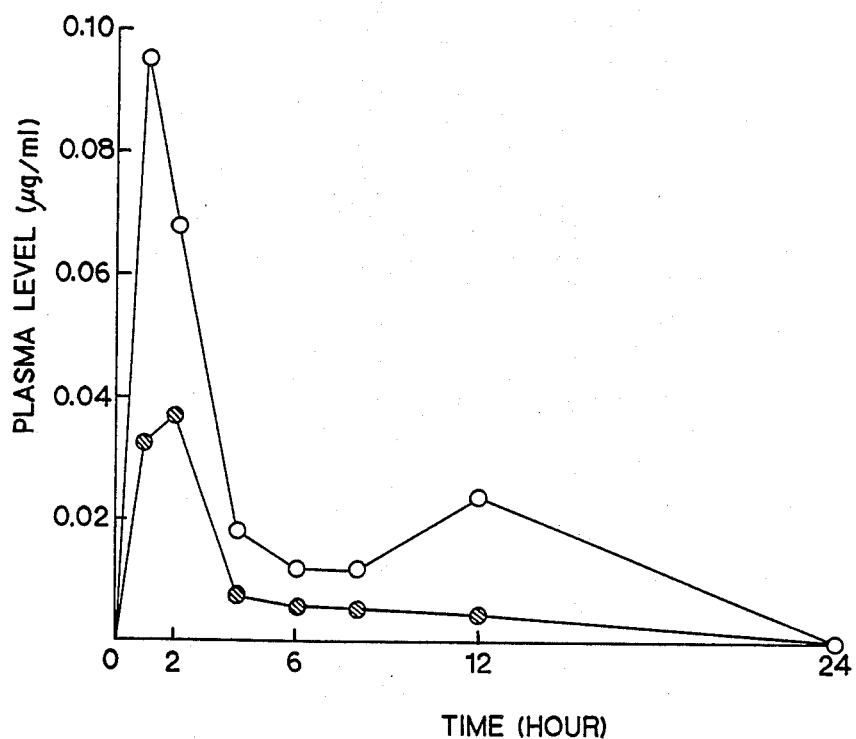
FIG. 2 represents the beagle plasma level curves of 7-hydroxy-3-phenyl-4H-1-benzopyran-4-one obtained in Test Example 7. Thus, o—o and ●—● depict the beagle plasma level curves of 7-hydroxy-3-phenyl-4H-1-benzopyran-4-one after oral administration of the ground mixture and 7-isopropoxy-3-phenyl-4H-1-benzopyran-4-one per se, respectively.

The results of both tests are given in Table 6 and FIG. 2.

TABLE 6

| | A.U.C. (μg · hr/ml) |
|---|---|
| Drug alone | 0.152 |
| Ground mixture | 0.485 |

As is evident from Table 6 and FIG. 2, the area under the blood level curve (A.U.C.) for the ground mixture was about three times as large as the drug alone.

We claim:

1. A ground mixture of an amorphous drug and an activated charcoal, wherein said mixture is prepared by grinding a poorly soluble crystalline drug and an activated charcoal.

2. A ground mixture according to claim 1, wherein the activated charcoal has an adsorption ability of not less than 0.15 cm$^3$/g as measured by the methanol adsorption method.

3. A ground mixture according to claim 1, wherein the activated charcoal has an adsorption ability of 0.15 to 1.50 cm$^3$/g as measured by the methanol adsorption method.

4. A ground mixture according to claim 1, wherein the drug has a solubility in water of less than $1 \times 10^{-3}$ g/ml.

5. A ground mixture according to claim 1, wherein the ratio of the activated charcoal to the activated charcoal plus the drug is 20 to 60% (w/w).

6. A ground mixture according to claim 1, wherein the ratio of the activated charcoal to the activated charcoal plus the drug is 30 to 50% (w/w).

7. A method for rendering a poorly soluble crystalline drug amorphous, which comprises grinding a mixture of said poorly soluble crystalline drug and an activated charcoal.

8. A method according to claim 7, wherein the ratio of the activated charcoal to the activated charcoal plus the drug is 30 to 50% (w/w).

9. A method according to claim 7, wherein an apparatus for the grinding is a vibrating mill.

* * * * *